United States Patent
Liu et al.

(10) Patent No.: US 11,077,293 B2
(45) Date of Patent: Aug. 3, 2021

(54) ANTIMICROBIAL INSERTS FOR STOPCOCK MEDICAL CONNECTORS

(71) Applicant: Becton, Dickinson and Company, Franklin Lakes, NJ (US)

(72) Inventors: Huibin Liu, West Jordan, UT (US); Bryan Fred Bihlmaier, Provo, UT (US); Janice Lin, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 30 days.

(21) Appl. No.: 15/986,352

(22) Filed: May 22, 2018

(65) Prior Publication Data

US 2018/0264250 A1   Sep. 20, 2018

Related U.S. Application Data

(63) Continuation of application No. 14/606,829, filed on Jan. 27, 2015, now Pat. No. 10,004,890.

(51) Int. Cl.
| | |
|---|---|
| *F16K 31/50* | (2006.01) |
| *F16K 11/072* | (2006.01) |
| *F16K 25/00* | (2006.01) |
| *A61M 39/16* | (2006.01) |

(Continued)

(52) U.S. Cl.
CPC .......... *A61M 39/162* (2013.01); *A61M 39/16* (2013.01); *A61M 39/22* (2013.01); *A61M 39/223* (2013.01); *F16K 11/072* (2013.01); *F16K 25/005* (2013.01);

(Continued)

(58) Field of Classification Search
CPC ............... A61M 39/162; A61M 39/22; A61M 2039/229; A61M 2039/1033; A61M 2039/027; A61M 2039/0285; A61M 2205/0205; F16K 5/04; F16K 5/0407; F16K 5/045; F16K 47/04; F16K 47/045; F16K 47/14
See application file for complete search history.

(56) References Cited

U.S. PATENT DOCUMENTS

| | | | |
|---|---|---|---|
| 4,540,025 A | * | 9/1985 | Ledeen ................. F16K 47/045 137/625.32 |
| 4,932,948 A | | 6/1990 | Kemes et al. |
| 5,046,528 A | | 9/1991 | Manska |

(Continued)

FOREIGN PATENT DOCUMENTS

| | | | |
|---|---|---|---|
| CH | 629579 A5 | * 4/1982 | ........... F16K 5/0407 |
| CN | 1242781 | 1/2000 | |

(Continued)

OTHER PUBLICATIONS

Merriam Webster (available online at https://www.merriam-webster.com/dictionary/proximal, accessed Jul. 23, 2019) (Year: 2019).

*Primary Examiner* — Hailey K. Do
(74) *Attorney, Agent, or Firm* — Kirton & McConkie; Craig Metcalf; Kevin Stinger

(57) ABSTRACT

Various embodiments of an antimicrobial insert for a stopcock medical connector are provided. More specifically, the present invention relates to an antimicrobial insert that is seated within at least a portion of the annular bore of the connector's tap, wherein fluid within the annular bore contacts the antimicrobial insert, thereby preventing microbial proliferation within the stopcock medical connector.

6 Claims, 14 Drawing Sheets

(51) Int. Cl.
*A61M 39/22* (2006.01)
*A61M 39/10* (2006.01)

(52) U.S. Cl.
CPC ... *F16K 31/502* (2013.01); *A61M 2039/1033* (2013.01); *A61M 2039/229* (2013.01)

(56) References Cited

U.S. PATENT DOCUMENTS

| | | |
|---|---|---|
| 5,135,026 A | 8/1992 | Manska |
| 5,203,775 A | 4/1993 | Frank et al. |
| 5,354,267 A | 10/1994 | Niermann et al. |
| 5,680,889 A * | 10/1997 | Boger ................. F16K 5/12 137/625.32 |
| 6,171,287 B1 | 1/2001 | Lynn et al. |
| 6,706,022 B1 | 3/2004 | Leinsing et al. |
| 7,033,339 B1 | 4/2006 | Lynn |
| 7,184,825 B2 | 2/2007 | Leinsing et al. |
| 7,232,428 B1 | 6/2007 | Inukai et al. |
| 7,771,383 B2 | 8/2010 | Truitt et al. |
| 8,048,034 B2 | 11/2011 | Eversull et al. |
| 8,591,471 B1 | 11/2013 | Marble |
| 8,715,222 B2 | 5/2014 | Truitt et al. |
| 10,149,971 B2 | 12/2018 | Liu et al. |
| 2003/0199835 A1 | 10/2003 | Leinsing et al. |
| 2004/0013703 A1 | 1/2004 | Ralph et al. |
| 2004/0089834 A1* | 5/2004 | Aoshima ............ F16K 5/04 251/288 |
| 2006/0016496 A1* | 1/2006 | Shane ............... E03C 1/086 137/801 |
| 2006/0089603 A1 | 4/2006 | Truitt et al. |
| 2007/0083188 A1 | 4/2007 | Grandt et al. |
| 2007/0119968 A1* | 5/2007 | Collins, Jr. ........ A61M 11/005 239/102.1 |
| 2007/0287953 A1 | 12/2007 | Ziv et al. |
| 2008/0161763 A1 | 7/2008 | Harding et al. |
| 2008/0194707 A1 | 8/2008 | Potter |
| 2008/0215021 A1 | 9/2008 | Cisko, Jr. et al. |
| 2009/0182309 A1 | 7/2009 | Muffly |
| 2010/0106102 A1 | 4/2010 | Ziebol et al. |
| 2010/0135949 A1 | 6/2010 | Ou-Yang |
| 2011/0257606 A1 | 10/2011 | Truitt et al. |
| 2012/0083750 A1 | 4/2012 | Sansoucy |
| 2012/0103448 A1 | 5/2012 | Hopf et al. |
| 2013/0012915 A1* | 1/2013 | Hopf ................. A61M 39/00 604/500 |
| 2013/0274686 A1 | 10/2013 | Ziebol et al. |
| 2014/0155844 A1 | 6/2014 | Isch et al. |
| 2014/0174578 A1 | 6/2014 | Bonnal et al. |
| 2014/0228466 A1 | 8/2014 | Lin et al. |
| 2014/0323970 A1* | 10/2014 | Duncan ............... A61M 5/165 604/136 |
| 2015/0126699 A1 | 5/2015 | Yarrison et al. |
| 2015/0231307 A1 | 8/2015 | Shevgoor et al. |
| 2015/0231309 A1 | 8/2015 | Bihlmaier et al. |
| 2015/0306370 A1 | 10/2015 | Liu et al. |
| 2016/0008569 A1 | 1/2016 | Harding |
| 2016/0213911 A1 | 7/2016 | Liu et al. |

FOREIGN PATENT DOCUMENTS

| | | | |
|---|---|---|---|
| CN | 102472401 | 5/2012 | |
| CN | 103013094 | 4/2013 | |
| DE | 4328095 A1 * | 2/1995 | ............ F16K 47/04 |
| DE | 19728562 C2 * | 12/2000 | ........... F16K 5/0605 |
| DE | 102009050590 A1 * | 4/2011 | ........... F16K 5/0407 |
| EP | 0166375 A2 * | 1/1986 | ............ F16K 1/222 |
| EP | 0410898 | 1/1991 | |
| EP | 1234596 | 8/2002 | |
| FR | 2791114 B1 * | 7/2002 | ........... B60H 1/3442 |
| GB | 1249484 A * | 10/1971 | ........... F16K 5/0407 |
| GB | 1262428 A * | 2/1972 | ........... F16K 5/0478 |
| JP | 63-020344 | 1/1988 | |
| JP | 02-234767 | 9/1990 | |
| JP | 03-029664 | 2/1991 | |
| JP | H08-141088 | 6/1996 | |
| JP | H08-508421 | 9/1996 | |
| JP | 08-280788 | 10/1996 | |
| JP | H11-70163 | 3/1999 | |
| JP | 2005530547 | 10/2005 | |
| JP | 2008-511371 | 4/2008 | |
| JP | 2008-517653 | 5/2008 | |
| JP | 2010-029381 | 2/2010 | |
| JP | 2010-179031 | 8/2010 | |
| JP | 2012-075901 | 4/2012 | |
| JP | 2012-523300 | 10/2012 | |
| JP | 2017513633 | 6/2017 | |
| JP | 2019155182 | 9/2019 | |
| WO | 94/22522 | 10/1994 | |
| WO | 97/35634 | 10/1997 | |
| WO | 2006/077951 | 7/2006 | |
| WO | 2011/006934 | 1/2011 | |
| WO | 2014/031774 | 2/2014 | |
| WO | 2015/126699 | 8/2015 | |
| WO | 2015/164130 | 10/2015 | |
| WO | 2015/164134 | 10/2015 | |

* cited by examiner

ANTIMICROBIAL INSERTS FOR STOPCOCK MEDICAL CONNECTORS

RELATED APPLICATIONS

This application is a continuation of U.S. application Ser. No. 14/606,829, filed Jan. 27, 2015, title ANTIMICROBIAL INSERTS FOR STOPCOCK MEDICAL CONNECTORS, which is incorporated herein in its entirety.

BACKGROUND OF THE INVENTION

Infusion therapy generally involves the administration of a medication intravenously. When performing a typical infusion therapy, one or more infusion therapy device (e.g. tubing sets, catheters, etc.) are commonly used. In some instances, an infusion therapy device may include a stopcock medical connector to permit selective administration of a fluid through the infusion therapy device. The stopcock medical connector comprises a housing in which is rotatably seated a tap. The tap includes one or more fluid pathways that may be aligned (i.e., the open position) or misaligned (i.e., the closed position) within the housing to permit or prevent a fluid from passing through the housing. Thus, when administration of fluid is desired, the tap is rotated from the closed position to the open position to permit fluid to pass through the housing and into the patient via the infusion therapy device. Conversely, the tap is rotated to the closed position when it is desired to cease the administration of a fluid.

When in the closed position, fluid trapped within the fluid pathway of the stopcock medical connector remains stagnant. These stagnant conditions are ideal for growth and colonization of microbes, which may lead to subsequent microbial infection when the medical connector is opened and the fluid is infused into the patient.

Thus, while methods and systems currently exist for selectively administering fluid to a patient via the use of a stopcock medical connector, challenges still exist. Accordingly, it would be an improvement in the art to augment or replace current techniques with the systems and methods discussed herein.

BRIEF SUMMARY OF THE INVENTION

The present invention relates to various antimicrobial stopcock medical connectors. More specifically, the present invention relates to an antimicrobial insert that is seated within at least a portion of the annular bore of the connector's tap, wherein fluid within the annular bore contacts the antimicrobial insert, thereby preventing microbial proliferation within the stopcock medical connector.

Some implementations of the present invention comprise a stopcock medical connector having two or more ports coupled to a housing, the housing further comprising a tap rotatably positioned therein. The tap further comprises one or more annular bores providing a pathway through the tap, wherein the tap may be rotated within the housing to align the one or more annular bores with the two or more ports of the housing, thereby providing fluid communication between two or more ports via the annular bores.

Some implementations of the present invention further comprise one or more antimicrobial inserts that is placed within at least one of the annular bores so as to be in contact with a fluid passing through the annular bore. As such, fluid passing through the stopcock medical connector is exposed to the antimicrobial insert. In some instances, the antimicrobial insert comprises a polymer material having an antimicrobial coating applied to the outer surface of the antimicrobial insert. In other instances, the antimicrobial insert comprises an antimicrobial material. Further, in some instances the antimicrobial insert comprises a polymer material forming a matrix comprising a plurality of interstices in which antimicrobial material is loaded or dispersed and is therefore capable of eluting out of the polymer material when the antimicrobial insert is exposed to a fluid.

Some implementations of the present invention comprise an antimicrobial material or coating having an antimicrobial agent selected from the group consisting of chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element. In other implementations, the antimicrobial material or coating comprises two or more antimicrobial agents. In some embodiments, the antimicrobial material is mixed into a carrying material, such as an adhesive, that is used for bonding the antimicrobial insert within the annular bore of the stopcock.

The antimicrobial insert of the present invention generally comprises a structure that is capable of being inserted and retained within the annular bore of the stopcock connector tap. In some instances, the antimicrobial insert comprises an annular shape having an outer diameter that is approximately equal to the inner diameter of the annular bore in which it is seated. For example, in some instances the antimicrobial insert comprises an outer diameter is approximately equal to the diameter of the annular bore, such that the antimicrobial insert is retained within the annular bore via a friction fit.

In some instances, the antimicrobial insert comprises a resilient polymer material having an initial, non-annular shape that is capable of being forced into the annular bore. Once inserted, the non-annular shape conforms to the annular shape of the annular bore and provides increased mechanical and frictional force on the annular bore as the resilient polymer material tries to resume its non-annular shape.

Some implementations of the present invention further comprise an antimicrobial insert comprising a plurality of interconnected structural members forming a grid-like structure forming a plurality of windows. An outer circumference of the grid-like structure is approximately equal to the diameter of the annular bore such that the antimicrobial insert is capable of being inserted therein. The grid-like structure further provides increased surface area as it is capable of extending throughout the entire length of the annular bore. The plurality of windows permits fluid to flow freely through the grid-like structure without compromising or reducing fluid flow. In some instances, the grid-like structure comprises a resilient polymer material whereby the antimicrobial insert is capable of being forced into the annular bore and maintained in its position through mechanical and frictional forces.

Some implementations of the present invention further include a stopcock medical connector comprising a tap having two or more annular bores, and further comprising two or more antimicrobial inserts positioned therein.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The present invention relates to various antimicrobial stopcock medical connectors. More specifically, the present invention relates to an antimicrobial insert that is seated within an annular bore of the connector's tap, wherein fluid within the annular bore contacts the antimicrobial insert, thereby preventing microbial proliferation within the stopcock medical connector.

Figure 1:
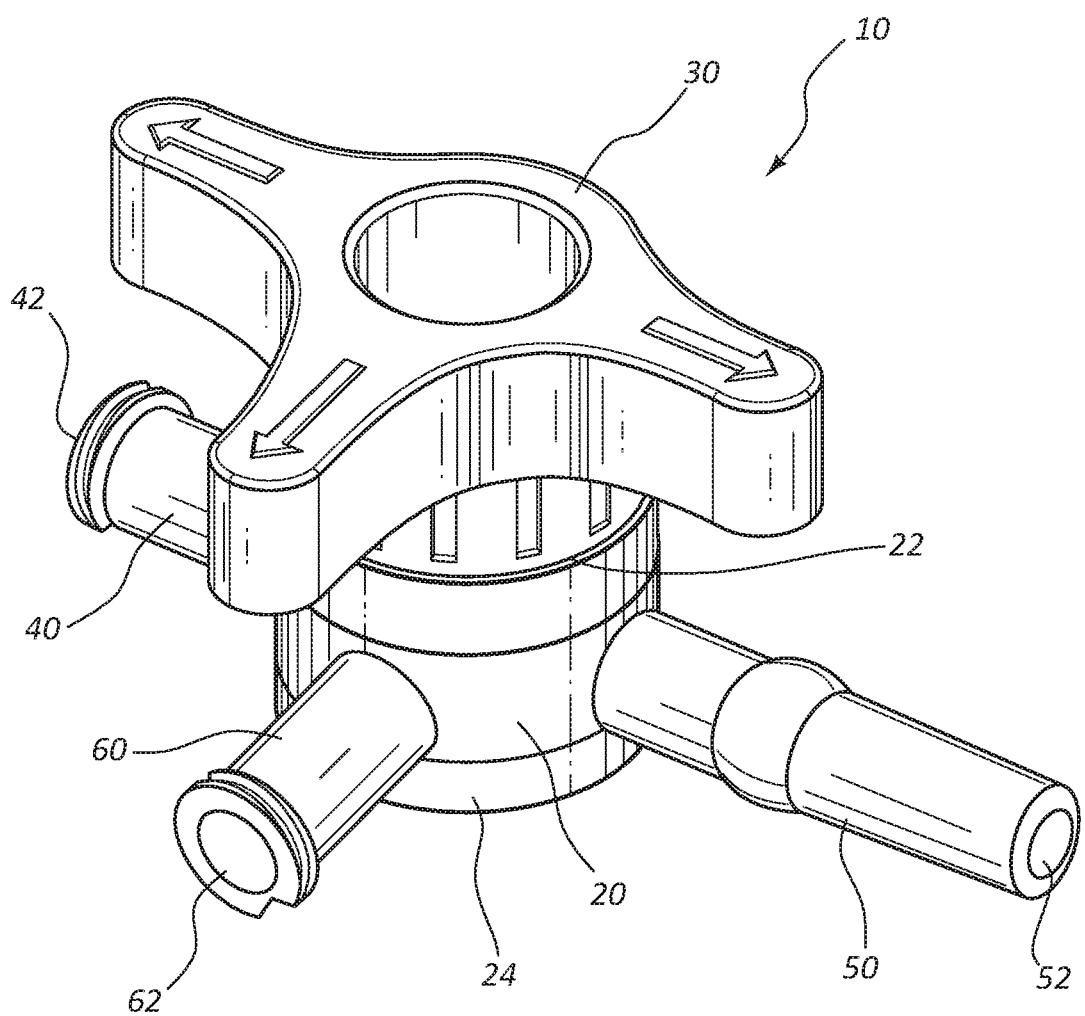
FIG. 1 shows a perspective view of a three-way antimicrobial stopcock medical connector in accordance with a representative embodiment of the present invention.
Figure 2:
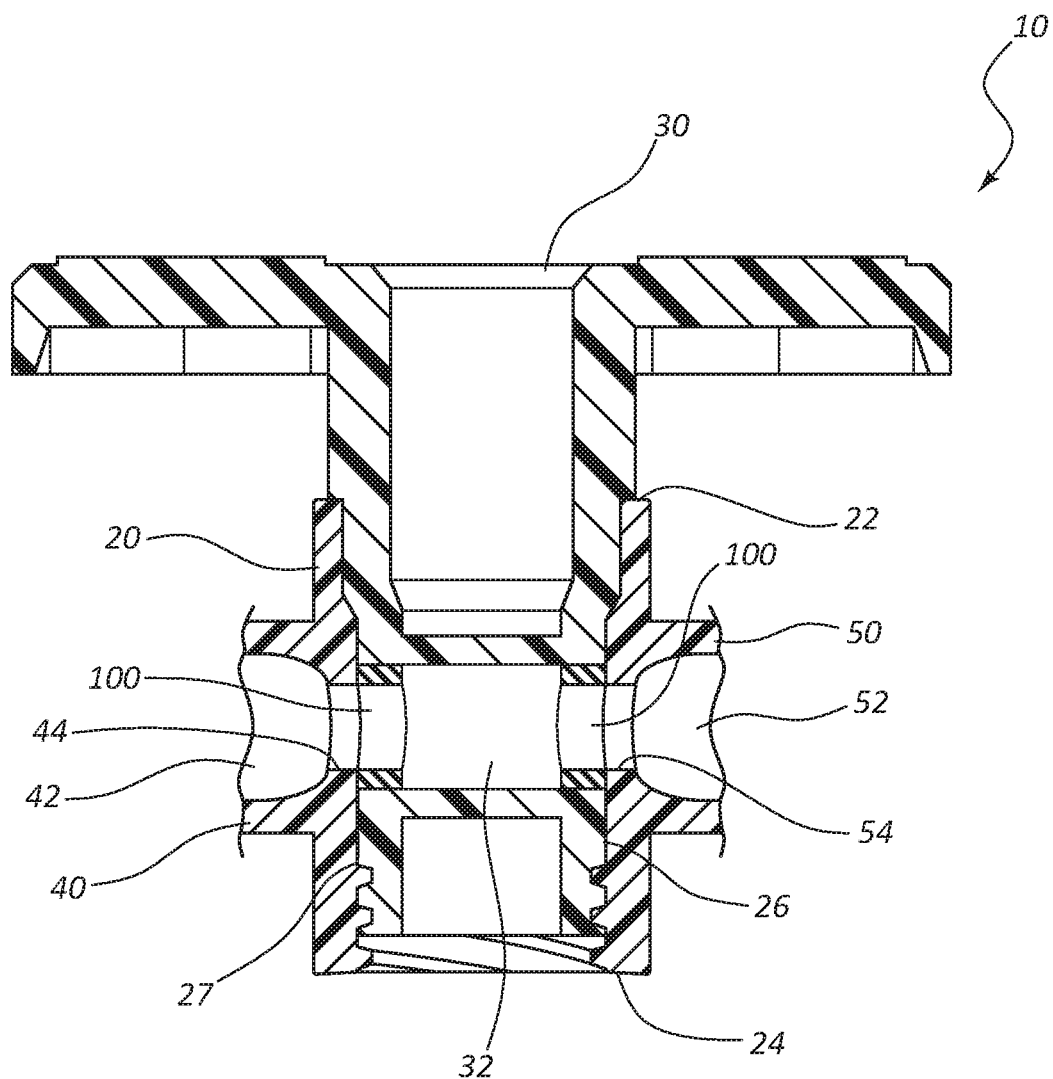
FIG. 2 shows a cross-section side view of an antimicrobial stopcock medical connector in an open position in accordance with a representative embodiment of the present invention.

Referring now to FIG. 1, a perspective view of a stopcock medical connector 10 is shown. Stopcock medical connector 10 comprises a housing 20 generally having a tubular shape. Housing 20 comprises an opening or proximal end 22 that is sized to compatibly receive tap 30. In some instances, housing comprises a side port of an intravenous device, such as a catheter adapter. Housing 20 further comprises a closed or distal end 24 that is located opposite opening 22, wherein housing 20 comprises a lumen 26 extending between proximal and distal ends 22 and 24, as shown in FIG. 2. In some instances, distal end 24 further provides a seat surface 27 that is configured to support tap 30 when seated within lumen 26.

Referring now to FIGS. 1 and 2, in some instances housing 20 further comprises one or more ports that are connected to housing 20 and in fluid communication with lumen 26. For example, in some embodiments housing 20 comprises an upstream port 40 and a downstream port 50. Housing 20 may further comprise a side port 60 to provide a 3-way stopcock medical connector. Embodiments of the present invention may alternatively comprise a 2-way stopcock medical connector.

Ports 40, 50 and 60 each comprise a hollow interior, 42, 52, and 62, respectively, which is in fluid communication with lumen 26. The free ends of ports 40, 50 and 60 may be coupled to an intravenous device, such as a section of intravenous tubing, or a syringe. Fluid within any of the ports may pass into another port by passing through annular bore 32 of tap 30. For example, fluid within upstream port 40 may flow into downstream port 50 via annular bore 32 when annular bore 32 is aligned with, and in fluid communication with ports 40 and 50. Similarly, fluid within upstream port 40 may flow into side port 60 when annular bore 32 is either aligned with, and in fluid communication with the ports 40 and 60. In some embodiments, annular bore 32 further comprises a secondary bore 33 (shown in FIGS. 4, 7 and 8) that intersect with, and is in fluid communication with annular bore 32. As such, fluid within upstream port 40 may flow into side port 60 when each of annular bore 32 and secondary bore 33 are in fluid communication with one of ports 40 and 60. Alignment of annular bore 32, secondary bore 33, and ports 40, 50 and 60 is achieved by rotating tap 30 within lumen 26, as is common to the operation of stopcock medical connectors.

Embodiments of the present invention further comprise an antimicrobial insert that is configured for insertion within one or more annular bores of tap 30. An antimicrobial insert is generally positioned within one or more annular bores of tap 30 so as to be in contact with a fluid that is present within, or passing through the one or more annular bores. As such, the antimicrobial insert kills microorganisms or inhibits their growth within the fluid.

The antimicrobial insert may comprise any compatible material. In some instances, an antimicrobial insert comprises a non-porous polymer material having an antimicrobial coating applied to the outer surface of the insert, wherein the antimicrobial coating comprises an antimicrobial agent that is safe for use in accordance with the teachings of the present invention. In other instances, an antimicrobial insert comprises a porous polymer material having an antimicrobial coating applied to the outer surface and infused within the porous structure of the insert, wherein the infused portion of the antimicrobial coating is capable of leaching out of the insert's porous structure to provide a zone of inhibition around the insert. Further still, in some instances an antimicrobial insert comprises a polymer material that is prepared in combination with an antimicrobial agent, whereby the final material comprises antimicrobial properties. Thus, the final material exhibits antimicrobial activity through direct contact with a fluid.

Some antimicrobial coatings of the present invention comprise one or more antimicrobial agents that are compatible for intravenous use. For example, in some instance an antimicrobial agent is selected from the group consisting of chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element. In some instances, the antimicrobial coating comprises two or more antimicrobial agents.

In some embodiments, the antimicrobial insert comprises an insoluble, cured antimicrobial coating. In other instances, the antimicrobial insert comprises a cured coating that is softened when exposed to fluid, thereby eluting a portion of the antimicrobial agent into the fluid. In other instances, the antimicrobial insert comprises a soluble antimicrobial coating that slowly dissolves upon prolonged exposure to a fluid.

In other instances, the final material of the antimicrobial insert elutes antimicrobial agent when contacted by a fluid, thereby providing a zone of inhibition surrounding the material. For example, in some embodiments an antimicrobial insert comprises a UV cured, hydrophilic polymer material that forms a matrix comprising a plurality of microscopic interstices in which an antimicrobial agent is dispersed or loaded. Upon exposure to fluid, the polymer matrix is softened and penetrated by the fluid. The antimicrobial agent within the polymer matrix is eluted out of the matrix and into the fluid to form a zone of inhibition in proximity to the polymer matrix. Examples of suitable polymer materials are provided in U.S. patent application Ser. Nos. 12/397,760, 11/829,010, 12/476,997, 12/490,235, and 12/831,880, each of which is incorporated herein in their entireties.

Figure 3:
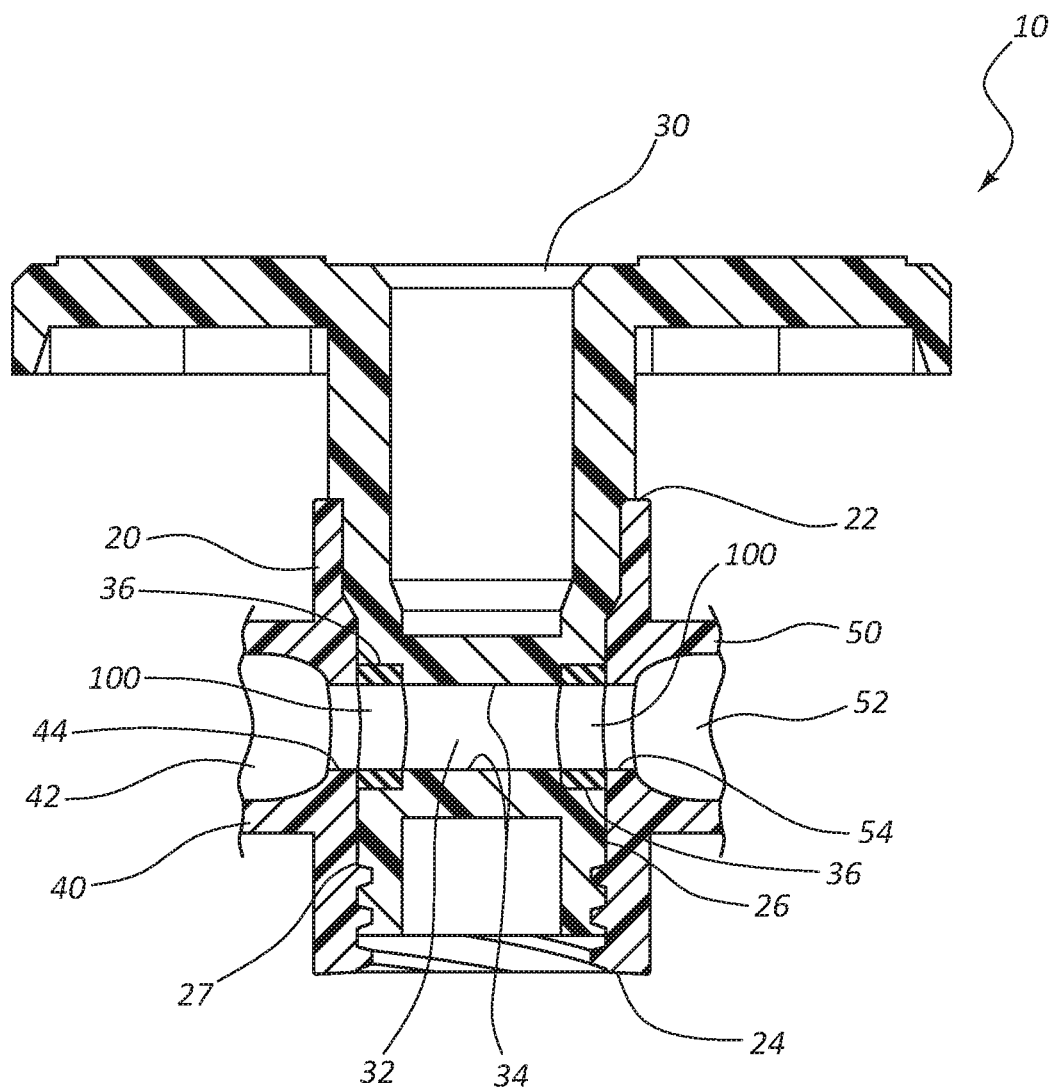
FIG. 3 shows a cross-section side view of an antimicrobial stopcock medical connector in an open position in accordance with a representative embodiment of the present invention.

With specific reference to FIGS. 2 and 3, stopcock medical connector 10 is shown with antimicrobial inserts 100 seated within a portion of annular bore 32. Antimicrobial inserts 100 may comprise any shape, cross-sectional shape, or size that is compatible for use in stopcock medical connector 10. As shown, in some embodiments antimicrobial inserts 100 comprise an annular ring having an outer diameter that is approximately equal to, or slightly larger than the diameter of annular bore 32, wherein antimicrobial inserts 100 are retained within annular bore 32 via a friction fit. In other instances, inserts 100 are retained within annular bore 32 via an adhesive.

In some instances, ports 40 and 50 comprise a narrowed diameter 44 and 54, respectively, which is smaller than the diameter of annular bore 32. For some embodiments, narrowed diameters 44 and 54 are approximately equal to an inner diameter of antimicrobial insert 100. As such, narrowed diameters 44 and 54 do not affect the flow of fluids through antimicrobial insert 100 and annular bore 32. Narrowed diameters 44 and 54 provide physical barriers to prevent displacement of antimicrobial inserts 100 into hollow interiors 42 and 52 of ports 40 and 50, respectively.

In some embodiments, annular bore 32 further comprises a stepped surface 34 that is flanked by antimicrobial inserts 100, as shown in FIG. 3. Stepped surfaces 34 provide channels 36 having a width configured to receive antimicrobial insert 100. In some instances, narrowed diameters 44 and 45 and stepped surfaces 34 combined to provide channels 36. Generally, stepped surfaces 34 have a height that is approximately equal to the cross-sectional thickness of antimicrobial insert 100. As such, the inner diameter of annular bore 32 at stepped surfaces 34 is approximately equal to the inner diameter of antimicrobial inserts 100. In this way, the passageway through tap 30, as defined by the inner diameter of antimicrobial inserts 100 and the inner diameter of annular bore 32 at stepped surfaces 34 is constant, and comprises a volume or diameter selected to provide a desired flow rate.

Figure 4:
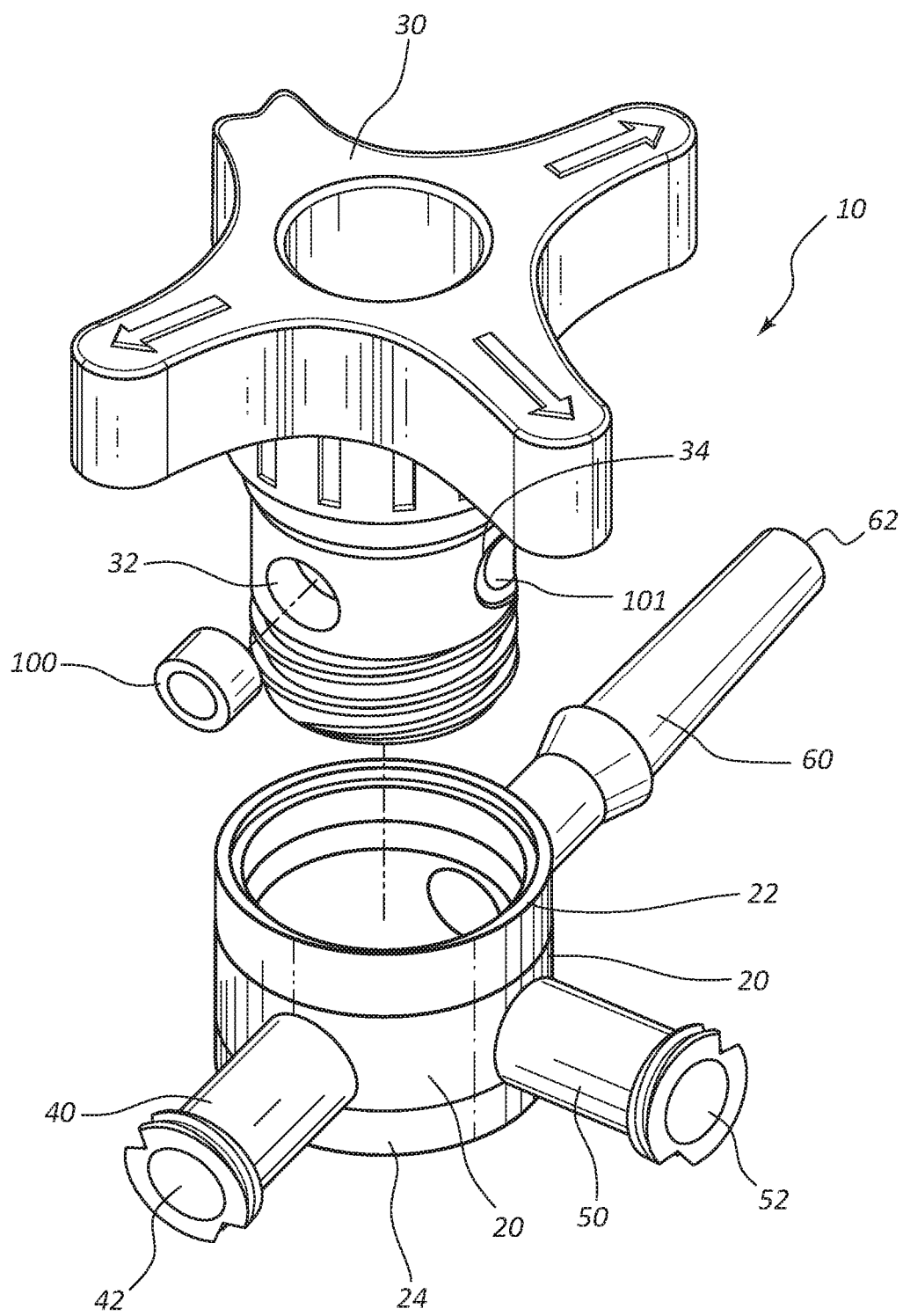
FIG. 4 shows a perspective, exploded view of 3-way antimicrobial stopcock medical connector in accordance with a representative embodiment of the present invention.

Referring now to FIG. 4, an exploded view of tap 30 and housing 20 is shown. In some instances, separate antimicrobial inserts 100 are provided for each annular bore of tap 30. For example, in some instances tap 30 comprises a pair of antimicrobial inserts 100 are inserted within annular bore 32 and a second antimicrobial insert 101 inserted within secondary annular bore 33. As such, fluid within housing 20 or tap 30 is in contact with at least one antimicrobial insert 100 regardless of the rotational position of tap 30.

Figure 5:
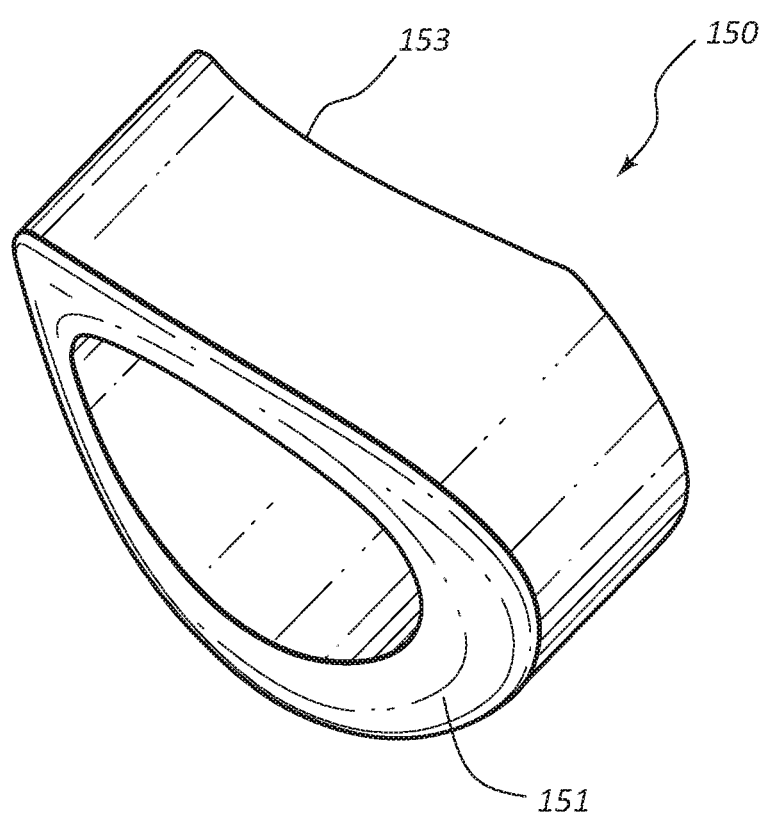
FIG. 5 shows a perspective view of an antimicrobial insert comprising a resilient polymer material and having a non-annular shape, wherein the antimicrobial insert assumes a temporary annular shape as it is forced into the annular bore of a tap and is maintained within the annular bore through frictional and mechanical forces in accordance with a representative embodiment of the present invention.

Referring now to FIG. 5, an antimicrobial insert 150 is shown. In some embodiments, antimicrobial insert 100 comprises an outer surface 151 having a convex surface with a radius that is approximately equal to, or equal to the radius of the outer surface of tap 30. As such, outer surface 151 and the outer surface of tap 30 provide a uniform surface in a common radial plane. In some instances, an inner surface 153 of antimicrobial insert 100 is planar. In other instances, inner surface 153 comprises a concave surface with a radius that is approximately equal to, or equal to the radius of the inner surface of tap 30.

In some instances, antimicrobial insert 150 comprises a resilient polymer material having an initial, non-annular shape that is capable of being forced into annular bore 32 of 30. Once inserted, the non-annular shape conforms to the annular shape of annular bore 32. The resilient forces within antimicrobial insert 150 provide increased mechanical and frictional force on annular bore 32 as the deformed antimicrobial insert 150 tries to resume its initial, non-annular shape. These increased mechanical and frictional forces maintain the position of antimicrobial insert 150 within annular bore 32 without requiring an adhesive or other retaining mechanism or structure.

Figure 6:
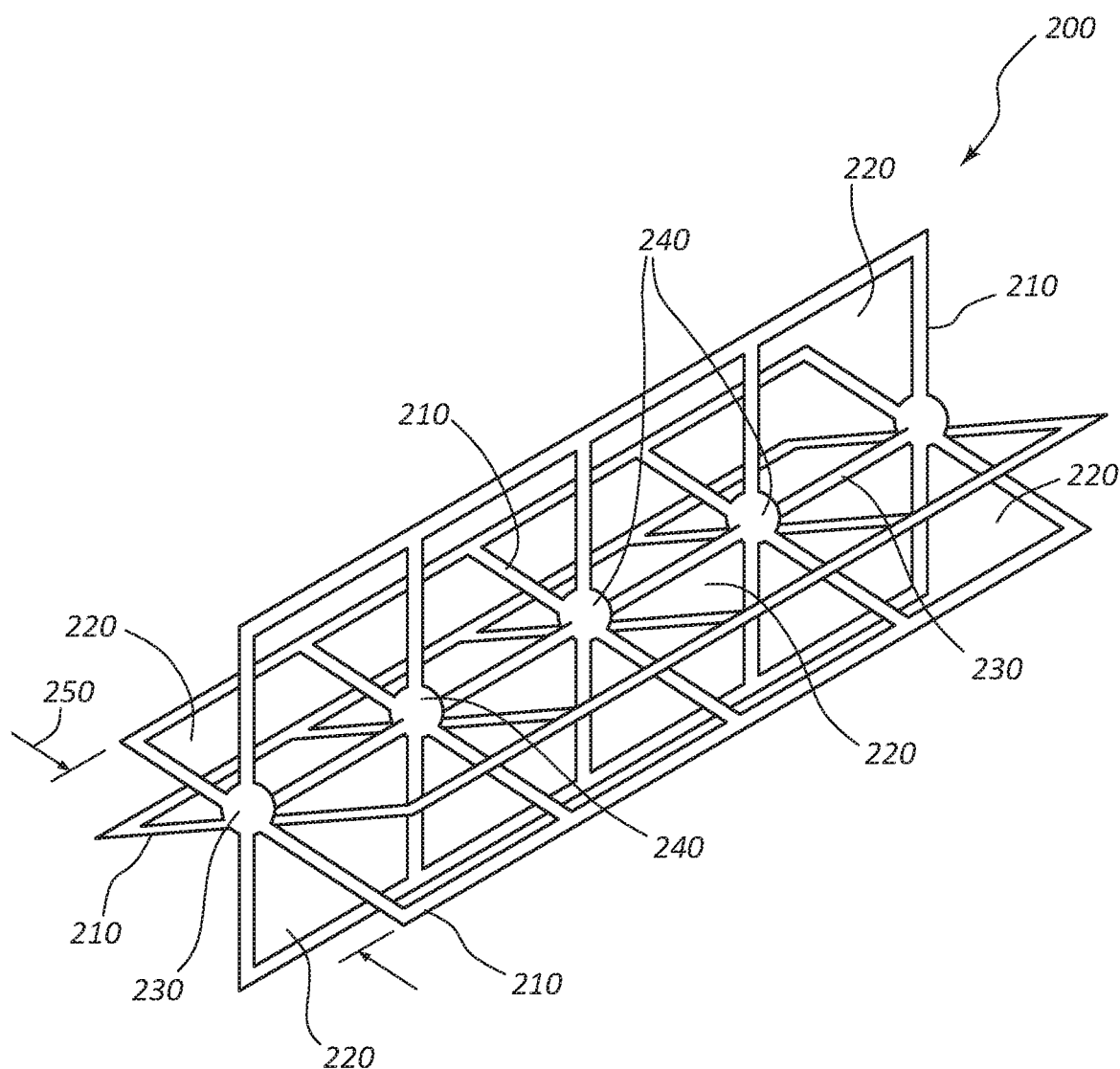
FIG. 6 shows a perspective view of an antimicrobial insert in accordance with a representative embodiment of the present invention.

Referring now to FIG. 6, an antimicrobial insert 200 is shown. Antimicrobial insert 200 comprises a monolithic structure forming a framework of interconnected segments 210. A plurality of windows 220 is provided between each of the interconnected segments 210, whereby the plurality of windows 220 provides a plurality of fluid pathways through and around the interconnected segments 210. In some instances, antimicrobial insert 200 comprises a central axis 230 running the entire length of antimicrobial insert 200. Central axis 230 further comprises a plurality of nodes 240 spaced between the proximal and distal ends of central axis 230, wherein the plurality of nodes 240 comprise a rigid joint of joined segments 210.

In some instances, antimicrobial insert 200 comprises a diameter 250 that is approximately equal to, or slightly smaller than the diameter of annular bore 32. As such, antimicrobial insert 200 is slidably inserted and retained within annular bore 32 in the same fashion as with antimicrobial insert 100. Antimicrobial insert 200 may comprise any material and/or coating in accordance with the present invention. For example, in some instances antimicrobial insert 200 comprises a polymer material having an antimicrobial coating applied to an outer surface of the insert. In other instances, antimicrobial insert 200 comprises an antimicrobial material. Antimicrobial insert 200 may further comprise a resilient polymer material whereby insert 200 is capable of being forced into annular bore 32, whereby insert 200 is slightly deformed upon insertion therein. In some instances, the forced-fit of antimicrobial insert 200 provides increased mechanical and frictional forces between insert 200 and annular bore 32, whereby the position of insert 200 within annular bore 32 is maintained by these forces without requiring an adhesive or other mechanical structures.

Figure 7:
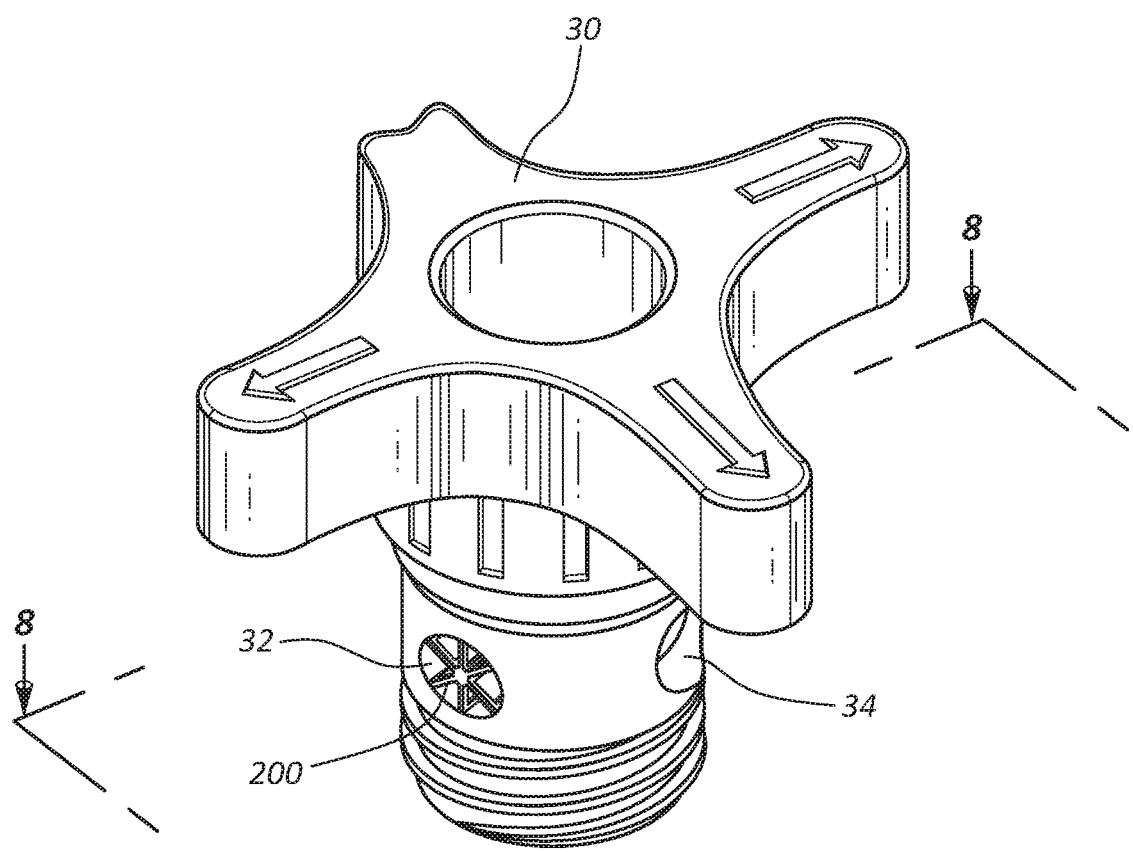
FIG. 7 shows a perspective view of a stopcock tap comprising an annular bore in which is seated the antimicrobial insert shown in FIG. 6, in accordance with a representative embodiment of the present invention.
Figure 8:
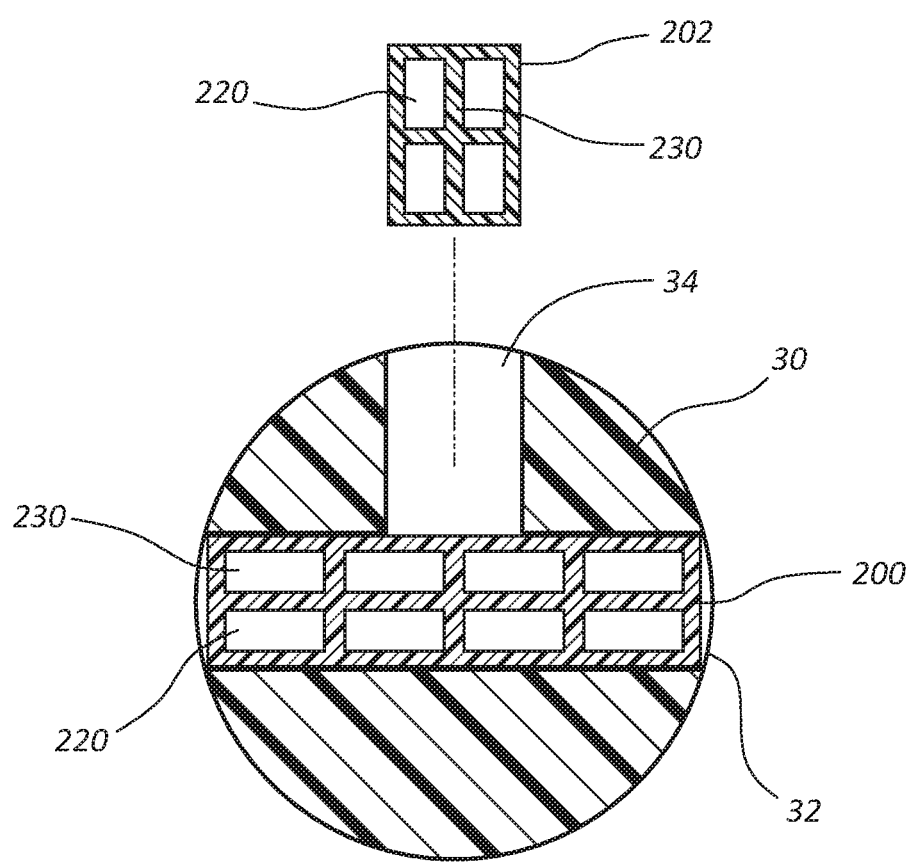
FIG. 8 shows a cross-section top view of the stem portion of the stopcock tap shown in FIG. 7, wherein one annular bore of the 3-way antimicrobial stopcock medical connector is fitted with the antimicrobial insert of FIG. 6, and an intersecting annular bore of the 3-way antimicrobial stopcock medical connector is shown ready to receive a shortened or truncated antimicrobial insert of FIG. 6 in accordance with a representative embodiment of the present invention.

Referring now to FIGS. 7 and 8, tap 30 is shown having antimicrobial insert 200 inserted within annular bore 32. In some instances, tap 30 comprises a single antimicrobial insert 200, wherein annular bore 34 does not have an insert. In other instances, tap 30 comprises a first antimicrobial insert 200 inserted within annular bore 32, and further comprises a truncated annular insert 202 inserted within annular bore 34, as shown in the cross-section view of FIG. 8. Further, in some instances annular bore 34 comprises more than two antimicrobial inserts.

Figure 9:
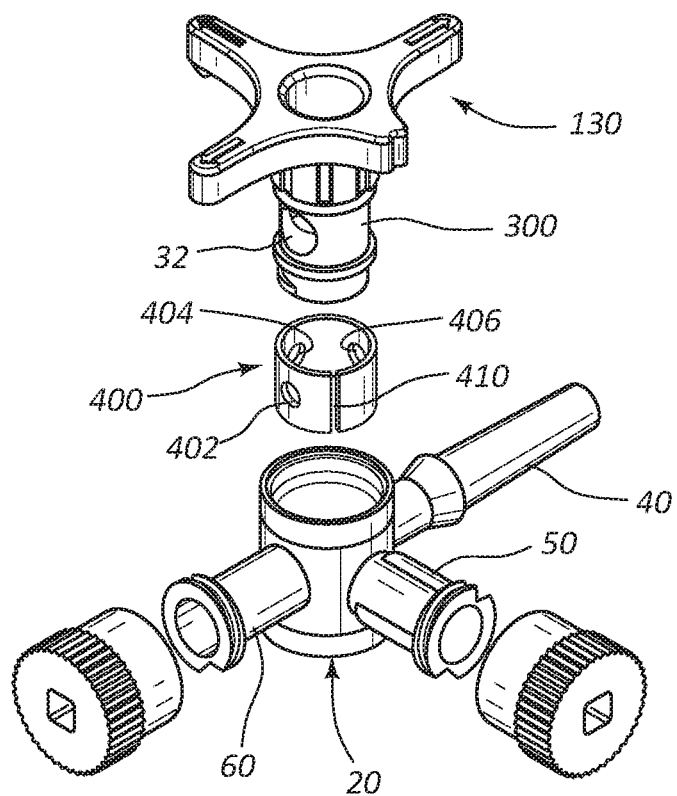
FIG. 9 shows an exploded view of a 3-way antimicrobial stopcock medical connector comprising a stopcock tap having a recessed, annular surface for receiving an antimicrobial ring in accordance with a representative embodiment of the present invention.
Figure 10:
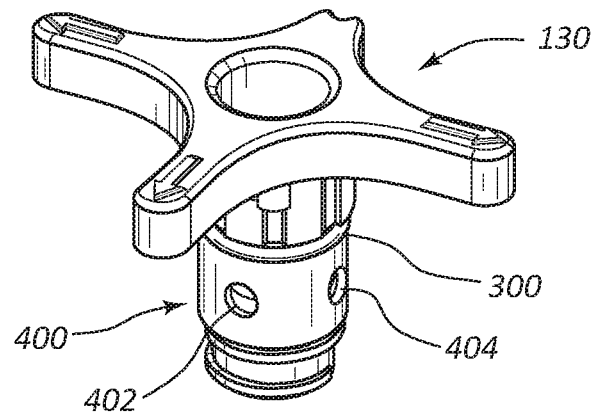
FIG. 10 shows a perspective view of the assembled 3-way antimicrobial stopcock medical connector shown in FIG. 9 in accordance with a representative embodiment of the present invention.

Some embodiments of the present invention further include a stopcock tap 130 comprising an annular recess 300 which encompasses annular bores 32 and 34 and is configured to receive antimicrobial ring 400, as shown in FIGS. 9 and 10. Antimicrobial ring 400 comprises, or is comprised of an antimicrobial material in accordance with the previous discussion. In some instances, antimicrobial ring 400 comprises a wall thickness that is less than or equal to the depth of annular recess 300, wherein placement of antimicrobial ring 400 within annular recess 300 provides stopcock tap 130 with a uniform outer diameter.

Antimicrobial ring 400 comprises fluid apertures 402, 404 and 406 that are provided and configured to align with annular bores 32 and 34 when installed within annular recess 300. In some instances, fluid apertures 402, 404 and 406 comprise a cross-sectional area that is less than a cross-sectional area of annular bores 32 and 34 so as limit the rate of flow through annular bores 32 and 34. In other instances, fluid apertures 402, 404 and 406 comprise cross-sectional areas that are equal to or larger than the cross-sectional areas of annular bores 32 and 34.

In some instances, antimicrobial ring 400 comprises a slit 410 to permit temporary expansion of antimicrobial ring 400 for the purpose of installing antimicrobial ring 400 within annular recess 300, as shown in FIGS. 9, 11, 12 and 14A. In some instances antimicrobial ring 400 comprises a resilient or inflexible material, or alternatively a resilient, flexible material that comprises a continuous circumference, such as is shown in FIG. 14B. As thus configured, antimicrobial ring may be temporarily deformed or stretched to be seated within annular recess 300, wherein antimicrobial ring 400 is restored to its original configuration once seated therein.

With continued reference to FIGS. 9 and 10, antimicrobial ring 400 may be retained within annular recess 300 by any known method or means. For example, in some instances antimicrobial ring 400 is retained within annular recess 300 via frictional and/or mechanical forces. In other instances antimicrobial ring 400 is retained within annular recess 300 via an adhesive or epoxy. In some instances annular recess 300 further comprises a physical feature that interacts either with slit 410 or a complimentary feature provided on the inner surface of antimicrobial ring 400. In this manner, the interaction between the physical feature and antimicrobial ring 400 maintains a preferred rotational positioning of antimicrobial ring 400 within annular recess 300.

Figure 11:
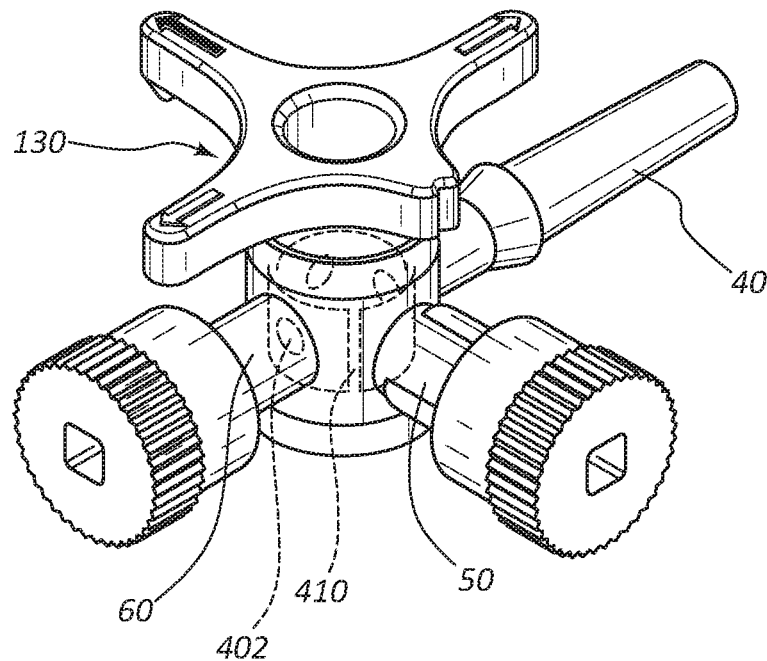
FIG. 11 shows a perspective top view of the 3-way antimicrobial stopcock medical connector shown in FIG. 9, wherein the stopcock tap has been rotated to close the fluid path to the side port in accordance with a representative embodiment of the present invention.
Figure 12:
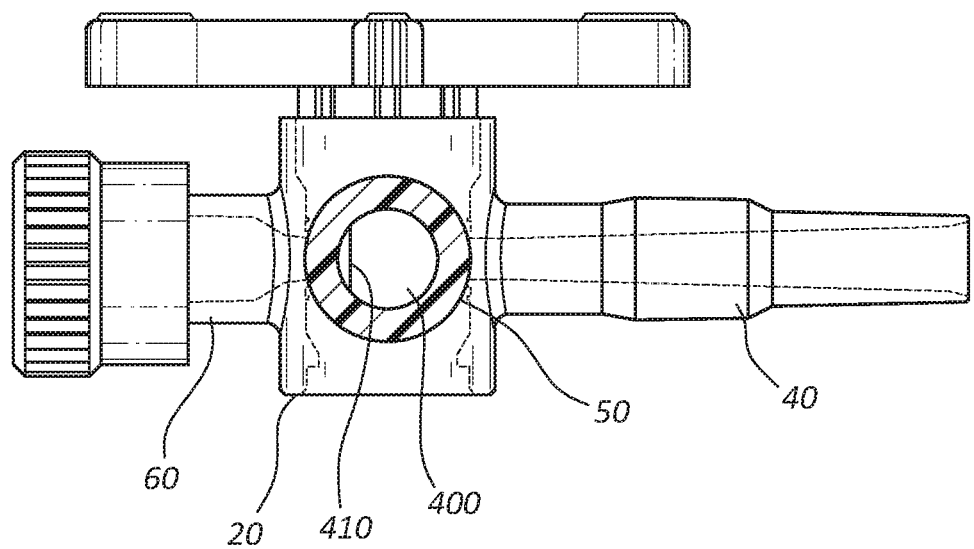
FIG. 12 shows a side plan view of the 3-way antimicrobial stopcock medical connector shown in FIG. 11, wherein the side port has been removed to provide a partial cross-section view into the housing in accordance with a representative embodiment of the present invention.
Figure 13:
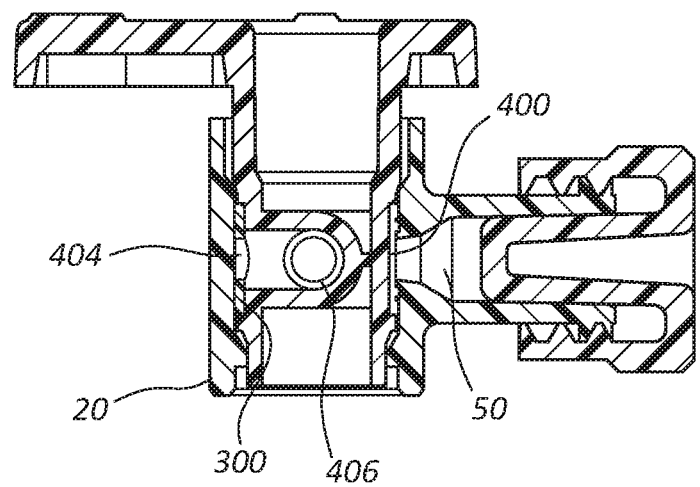
FIG. 13 shows a cross-section side view of the 3-way antimicrobial stopcock medical connector shown in FIG. 11 in accordance with a representative embodiment of the present invention.
Figures 14A, 14B:
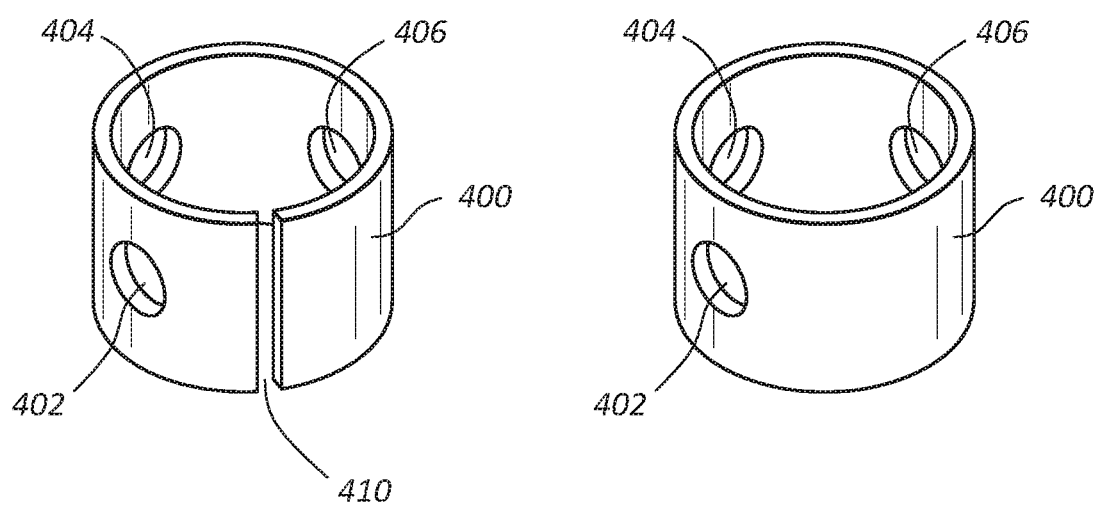
FIGS. 14A and 14B each show a perspective top view of an antimicrobial ring in accordance with representative embodiments of the present invention.
Figure 15:
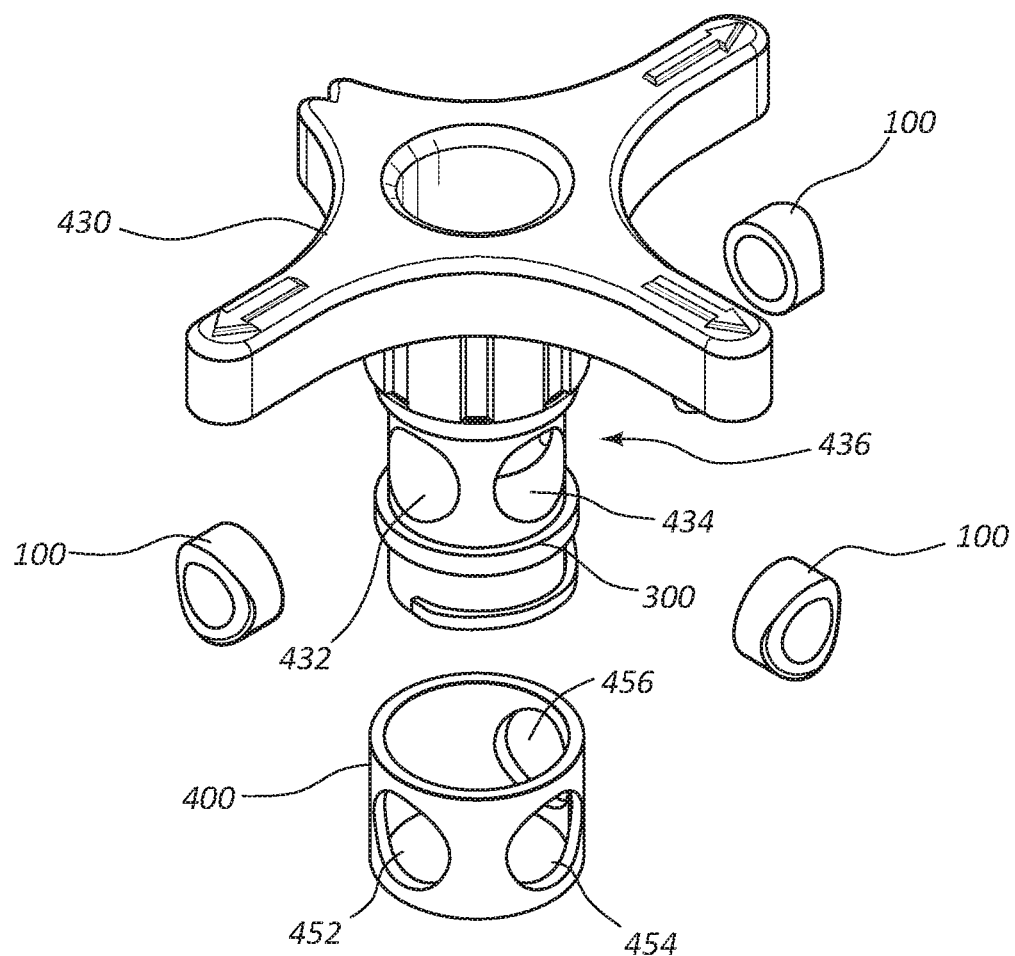
FIG. 15 shows an exploded view of a 3-way antimicrobial stopcock medical connector comprising an antimicrobial ring having bores configured to receive antimicrobial inserts in accordance with a representative embodiment of the present invention.

As with the previously discussed embodiments, the flow path of a fluid through stopcock medical adapter 10 may be selected by rotating stopcock tap 130 within housing 20 to align annular bore 32 with a desired port 40, and/or 60. In some instances, stopcock tap 130 is rotated to a position wherein bore 32 is aligned with upstream and downstream ports 40 and 60, and misaligned with side port 50, as shown in FIGS. 11-13. Fluid apertures 402 and 406 are aligned with downstream port 60 and upstream port 40, respectively. Fluid aperture 404 is not aligned with any port, but rather is in contact with the inner surface of housing 20, as can be seen in FIG. 13. The proximity and contact between the portion of antimicrobial ring 400 proximate to port 40 and the inner surface of housing 20 prevents antimicrobial growth that may otherwise occur in the stagnant fluid located between these components and/or surfaces. Similarly, side port 50 is not aligned with any fluid apertures, but rather is in contact with a portion of antimicrobial ring 400 positioned between adjacent fluid apertures 402 and 406, as can be seen in FIGS. 12 and 13. The proximity and contact between antimicrobial ring 400 and side port 50 prevents antimicrobial growth that may otherwise occur in stagnant fluids between these components and/or surfaces. Antimicrobial ring 400 therefore provides antimicrobial properties to any surface, interface, aperture, void, volume, or fluid in which it is in proximity and/or contact. Thus, depending upon the position of stopcock tap 130 within housing 20, antimicrobial ring 400 may provide antimicrobial protection to a plurality of surfaces, materials and fluids within, or passing through stopcock medical adapter 10.

Figure 16A:
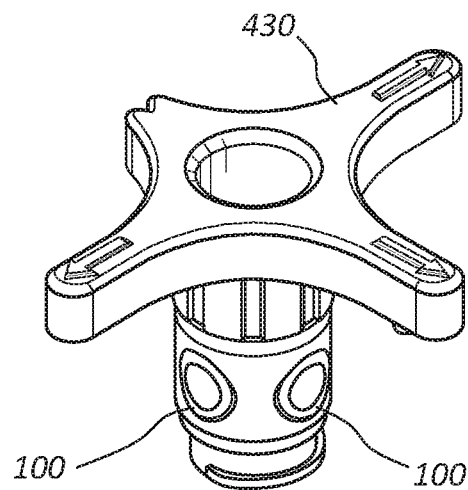
FIGS. 16A and 16B each show a perspective view of the assembled 3-way antimicrobial stopcock medical connector of FIG. 15 in accordance with representative embodiments of the present invention.
Figure 16B:
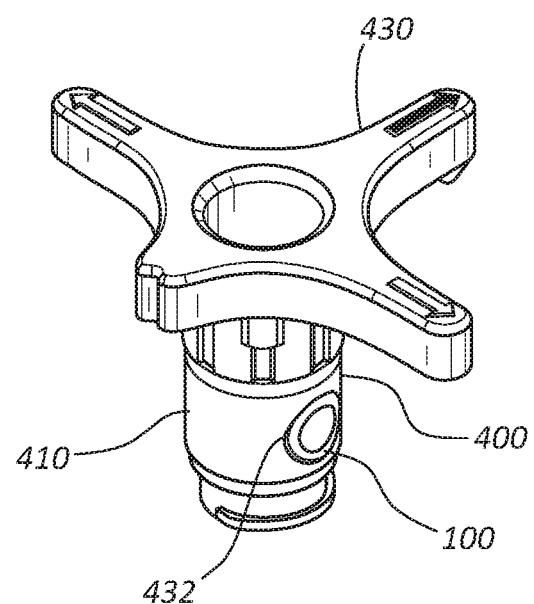
Figure 17:
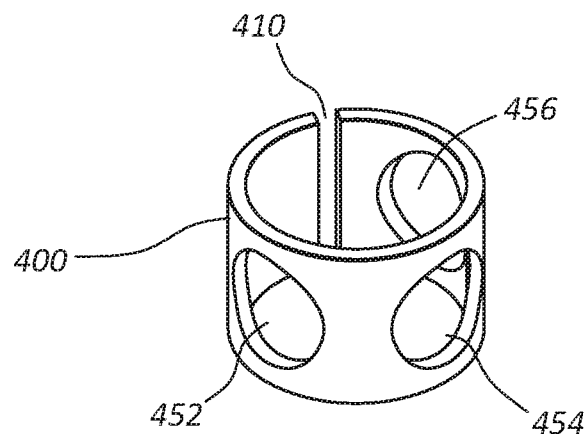
FIG. 17 shows a perspective view of the antimicrobial ring of FIG. 15 in accordance with a representative embodiment of the present invention.

Referring now to FIGS. 16A-17, in some embodiments stopcock tap 430 comprises oversized annular bores 432, 434 and 436. Oversized bores 432, 434 and 436 each comprise an inner diameter configured to receive an antimicrobial insert 100 to achieve maximum antimicrobial elution. In some instances, antimicrobial inserts 100 comprise a length that is greater than the depth of the oversized bores. As such, when antimicrobial inserts 100 are inserted within oversized bores 432, 434 and 436, the outer or end face surfaces of inserts 100 protrude outwardly beyond annular recess 300. In some instances, antimicrobial ring 400 comprises enlarged ports 452, 454, and 456 each comprising an inner diameter configured to receive the protruding surfaces of antimicrobial inserts 100. In some instances, antimicrobial ring 400 comprises a wall thickness that is approximately equal to the height of the protruding end face of antimicrobial inserts 100. Further, in some instances the end faces of antimicrobial inserts 100 comprise a radius that is equal to, or approximately equal to the radius of the outer surface of antimicrobial ring 400. As such, when antimicrobial ring 400 is inserted or fitted within annular recess 300, and inserts 100 are fitted within enlarged ports 452, 454, and 456, the end faces of inserts 100 and the outer surface of antimicrobial ring 400 provide an even surface in a uniform radial plane. In some instances, the inner face surfaces of inserts 100 further comprise a radius that is equal to, or approximately equal to the radius of the inner surface of stopcock tap 430.

Figure 18:
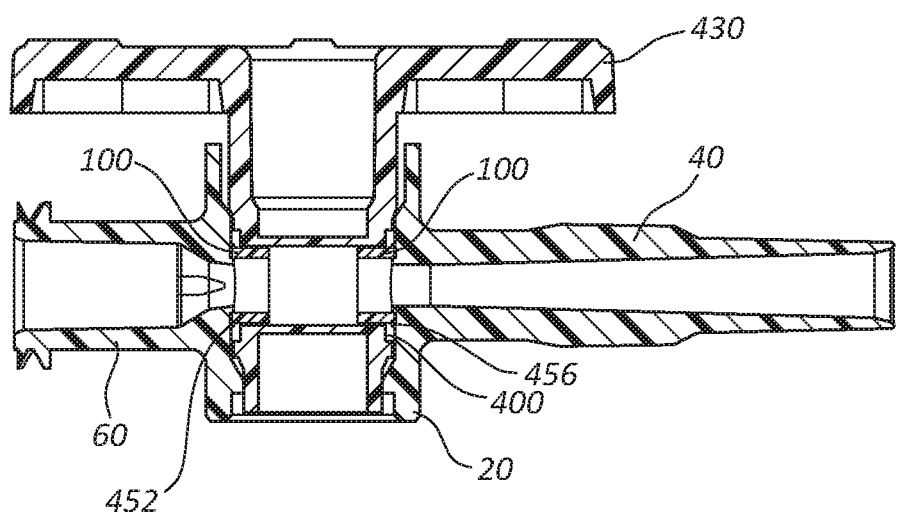
FIG. 18 shows a cross-section side view of the 3-way antimicrobial stopcock connector of FIG. 16 in accordance with a representative embodiment of the present invention.

In some embodiments, oversized bores 432, 434 and 436 comprise an inner stop (not show) to prevent over-insertion of inserts 100. In some instances, inserts 100 are fixedly secured within oversized bores 432, 434, and 436 via an adhesive or a mechanical or friction fit. In other instance, inserts 100 are maintained within their respective bores due to the minimal tolerance between the inner surface of housing 20 and the outer surface of antimicrobial ring 400 when tap 430 is inserted within housing 20, as shown in FIG. 18. In some instances, inserts 100 comprise an inner diameter configured to achieve a direct flow rate, as discussed previously.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A stopcock medical connector device, comprising:
   a housing, comprising an upstream port and a downstream port;
   a tap rotatably seated in the housing, wherein the tap comprises an annular bore configured to align with the upstream port and the downstream port; and
   an elongated structure disposed within the annular bore, wherein a diameter of the elongated structure is equal to a diameter of the annular bore, wherein the downstream port is configured to receive fluid from the upstream port through the annular bore and the elongated structure, wherein
   the elongated structure comprises an antimicrobial material, wherein the elongated structure comprises a central axis portion and a plurality of segments extending outwardly from the central axis portion.

2. The stopcock medical connector device of claim 1, wherein the antimicrobial material comprises an antimicrobial coating.

3. The stopcock medical connector device of claim 1, wherein the antimicrobial material is selected from the group consisting of chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element.

4. The stopcock medical connector device of claim 1, wherein a first pair of opposing segments of the plurality of segments are joined at an enlarged node, wherein a second pair of opposing segments of the plurality of segments are joined at the enlarged node.

5. The stopcock medical connector device of claim 1, wherein prior to insertion of the elongated structure into the annular bore, the diameter of the elongated structure is equal to the diameter of the annular bore.

6. The stopcock medical connector device of claim 1, wherein the elongated structure comprises a resilient polymer material, the elongated structure is deformed and fitted within the annular bore.

\* \* \* \* \*